(12) United States Patent
Nakaya

(10) Patent No.: US 11,234,847 B2
(45) Date of Patent: Feb. 1, 2022

(54) MEDICAL-DEVICE POSITION ADJUSTING METHOD AND MEDICAL DEVICE SYSTEM

(71) Applicant: TERUMO KABUSHIKI KAISHA, Tokyo (JP)

(72) Inventor: Shinsuke Nakaya, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 273 days.

(21) Appl. No.: 16/520,528

(22) Filed: Jul. 24, 2019

(65) Prior Publication Data

US 2019/0343667 A1    Nov. 14, 2019

Related U.S. Application Data

(62) Division of application No. 15/667,059, filed on Aug. 2, 2017, now Pat. No. 10,390,983.

(30) Foreign Application Priority Data

Aug. 2, 2016 (JP) .................................. 2016-152070

(51) Int. Cl.
*A61F 2/966* (2013.01)
*A61B 17/3207* (2006.01)
(Continued)

(52) U.S. Cl.
CPC ............ *A61F 2/966* (2013.01); *A61B 5/4851* (2013.01); *A61B 17/320725* (2013.01); *A61F 2/852* (2013.01); *A61F 2/958* (2013.01); *A61M 25/09041* (2013.01); *A61M 25/104* (2013.01); *A61B 1/005* (2013.01); *A61F 2002/826* (2013.01); *A61M 2025/0183* (2013.01); *A61M 2025/09008* (2013.01); *A61M 2025/09116* (2013.01); *A61M 2025/09125* (2013.01); *A61M 2025/109* (2013.01)

(58) Field of Classification Search
CPC ............ A61B 17/320725; A61B 1/005; A61B 5/4851; A61F 2002/826; A61F 2/852; A61F 2/958; A61F 2/966; A61M 2025/0183; A61M 2025/09008; A61M 2025/09116; A61M 2025/09125; A61M 2025/109; A61M 25/09041; A61M 25/104
See application file for complete search history.

(56) References Cited

U.S. PATENT DOCUMENTS 5,320,634 A * 6/1994 Vigil .............. A61B 17/320725
604/103.08
5,395,389 A 3/1995 Patel
(Continued)

*Primary Examiner* — Mohamed G Gabr
(74) *Attorney, Agent, or Firm* — Buchanan Ingersoll & Rooney PC

(57) ABSTRACT

A medical device system includes a medical device that is configured to be delivered to a lesion area in a body lumen, a guide wire that is configured to guide the medical device, a port member that is configured to introduce the guide wire and the medical device into a living body, a proximal-end fixing member that is configured to fix the guide wire and the port member and is provided with an operation unit that is configured to cause the guide wire to move in an insertion/pulling-out direction from the fixed state, an anchor device provided with an anchor portion in a distal portion thereof, and an anchor-device guide wire that is configured to guide the anchor device.

10 Claims, 9 Drawing Sheets

(51) Int. Cl.
*A61M 25/09* (2006.01)
*A61M 25/10* (2013.01)
*A61F 2/82* (2013.01)
*A61M 25/01* (2006.01)
*A61F 2/852* (2013.01)
*A61B 5/00* (2006.01)
*A61F 2/958* (2013.01)
*A61B 1/005* (2006.01)

(56) References Cited

U.S. PATENT DOCUMENTS

| | | |
|---|---|---|
| 2001/0056274 A1 | 12/2001 | Perkins et al. |
| 2006/0190025 A1* | 8/2006 | Lehe ................ A61B 17/12122 606/200 |
| 2018/0036158 A1 | 2/2018 | Nakaya |

* cited by examiner

MEDICAL-DEVICE POSITION ADJUSTING METHOD AND MEDICAL DEVICE SYSTEM

CROSS-REFERENCES TO RELATED APPLICATIONS

This application is a Divisional of U.S. application Ser. No. 15/667,059 filed on Aug. 2, 2017, and claims the benefit of Japanese Application No. JP2016-152070 filed on Aug. 2, 2016, the entire content of each of which is incorporated herein by reference.

TECHNICAL FIELD

The present invention relates to a medical-device position adjusting method and a medical device system used in the method, in which guide and insertion into a body lumen is performed along a guide wire.

BACKGROUND

Medical treatments for a vascular lesion which use a catheter are widely performed because they are less surgically invasive than other vascular lesion treatments. For example, in percutaneous transluminal coronary angioplasty, a balloon catheter is used to widen a lesion area of a coronary artery so as to improve bloodflow.

Progression of arterioscleosis results in calcification of the lesion area and forming of a hard site. In some such lesions, a dilation force of a balloon catheter is not sufficient to widen the calcified lesion area. As a medical device that is capable of performing treatment even in this case, it is known to use a scoring balloon catheter. The scoring balloon catheter has a knife-edge-shaped or linear blade provided on the balloon, and the blade produces cracks in the calcified site such that it is easy to dilate a lumen. In addition, other known devices for removing the calcified site or plaque include a cutter that rotates at a high speed, a rotary file, a transducer, and a laser cutter. One example of a balloon catheter provided with a blade is disclosed in U.S. Pat. No. 5,320,634.

SUMMARY

The lesion areas are not necessarily distributed in the entire region of a blood vessel in a circumferential direction, but may be distributed only in a part of the blood vessel in the circumferential direction. In particular, in a bent portion of the blood vessel, the lesion areas may be distributed only on an outer curved side of the bent portion, or only on an inner curved side of the bent portion.

The medical device is inserted into the lesion area while being guided by a guide wire that is inserted into the blood vessel in advance. The guide wire which is inserted into the bent portion of the blood vessel has a path that is limited, depending on, for example, a shape of the bent portion, or a state of the lesion area. In this manner, a position of the medical device in the bent portion is also limited, and thus it is may not be possible for the medical device to appropriately approach the lesion area. To address these and other issues, a medical-device position adjusting method and a medical device system used in the method are disclosed in which a path of a guide wire is changed in a blood vessel after insertion thereof, thereby making it possible to adjust a position of a medical device in the lesion area.

In an embodiment, there is provided a medical-device position adjusting method of adjusting a position of a medical device by adjusting a path of a guide wire inserted into a body lumen, the method including: a step of preparing a medical device that is delivered to a lesion area in the body lumen, a guide wire that guides the medical device, a port member that introduces the guide wire and the medical device into a living body, a proximal-end fixing member that fixes the guide wire and the port member and is provided with an operation unit that causes the guide wire to move in an insertion/pulling-out direction from the fixed state, an anchor device provided with an anchor portion in a distal portion thereof, and an anchor-device guide wire that guides the anchor device; a step of inserting the guide wire from the port member farther forward than the lesion area of the body lumen; a step of inserting the anchor device into the body lumen and fixing the guide wire to an inner wall surface of the body lumen by the anchor portion at a position farther forward than the lesion area; a step of inserting the medical device from the port member along the guide wire into the lesion area or a position in the vicinity of the lesion area; and a step of fixing the guide wire and the port member with the proximal-end fixing member, causing the guide wire to move in the insertion/pulling-out direction by using the operation unit, thereby, changing a path of the guide wire in the body lumen, and adjusting a position of the medical device in the lesion area.

In an embodiment, there is provided a medical device system including: a medical device that is delivered to a lesion area in a body lumen; a guide wire that guides the medical device; a port member that introduces the guide wire and the medical device into a living body; a proximal-end fixing member that fixes the guide wire and the port member and is provided with an operation unit that causes the guide wire to move in an insertion/pulling-out direction from the fixed state, an anchor device provided with an anchor portion in a distal portion thereof, and an anchor-device guide wire that guides the anchor device.

In the medical-device position adjusting method having such a configuration described above, it is possible to cause the guide wire to move to a hand-side position in the body lumen, and thus it is possible to adjust the position of the medical device to an appropriate position in the body lumen. In other words, in the medical-device position adjusting method, since it is possible to adjust the position of the medical device such that it is possible to exhibit the best performance of the medical device, and it is possible to smoothly insert the medical device to a desired position, it is possible to achieve improvement of efficacy of medical treatment and shortening of time for medical treatment.

In addition, the lesion area may be positioned in a bent portion of the body lumen. The guide wire may then be caused to move in the insertion/pulling-out direction by the operation unit, and thereby the path of the guide wire may be changed between an outer curved side and an inner curved side of the bent portion. In this manner, it is possible to reliably adjust the position of the medical device in the bent portion of the body lumen in which it is difficult to appropriately position the medical device.

In addition, in the step of inserting the medical device from the port member along the guide wire, the medical device may be inserted to a position in the vicinity in front of the lesion area. In the step of adjusting the position of the medical device in the lesion area, the path of the guide wire may be changed in the body lumen while the medical device is inserted to the position of the lesion area. In this manner, it is possible to perform the insertion into the body lumen while the medical device is disposed at an appropriate position.

In addition, the anchor portion as a balloon may be dilated, and the dilation of the balloon in the body lumen may cause the guide wire to be fixed to an inner wall surface of the body lumen. The method may further include a step of deflating and pulling out an anchor portion from the body lumen, after the step of changing the path of the guide wire in the body lumen and adjusting the position of the medical device in the lesion area. In this manner, it is possible to perform a function of fixing the guide wire in a simplified structure, and it is possible to easily collect the anchor portion from the lesion area.

In addition, the medical-device position adjusting method may further include: a step of causing the medical device to function in the lesion area, after the step of deflating and pulling out the anchor portion from the body lumen. In this manner, it is possible for the anchor device not to interfere with the function of the medical device.

In the medical device system having such a configuration described above, it is possible to cause the guide wire to move to a hand-side position in the body lumen, and thus it is possible to adjust the position of the medical device to an appropriate position in the body lumen. In other words, in the medical device system, since it is possible to adjust the position of the medical device such that it is possible to exhibit the best performance of the medical device, and it is possible to smoothly insert the medical device to a desired position, it is possible to achieve improvement of efficacy of medical treatment and shortening of time for medical treatment.

In addition, the proximal-end fixing member may be provided with a port-member fixing portion to which the port member is fixed, a guide-wire fixing portion to which the guide wire is fixed, and a medical-device guiding portion that guides the medical device in a direction different from the insertion/pulling-out direction of the guide wire. In this manner, it is possible not to interfere with the insertion of the medical device while the port member and the guide wire are fixed.

In addition, the guide-wire fixing portion may be provided with a holding portion that holds and fixes the guide wire, and the operation unit that causes the holding portion to move in the insertion/pulling-out direction with respect to the port member. In this manner, an operator can move the guide wire in the insertion/pulling-out direction through an operation of the operation unit, and it is possible to reliably perform fine adjustment of the movement of the guide wire.

DETAILED DESCRIPTION

Figure 1:
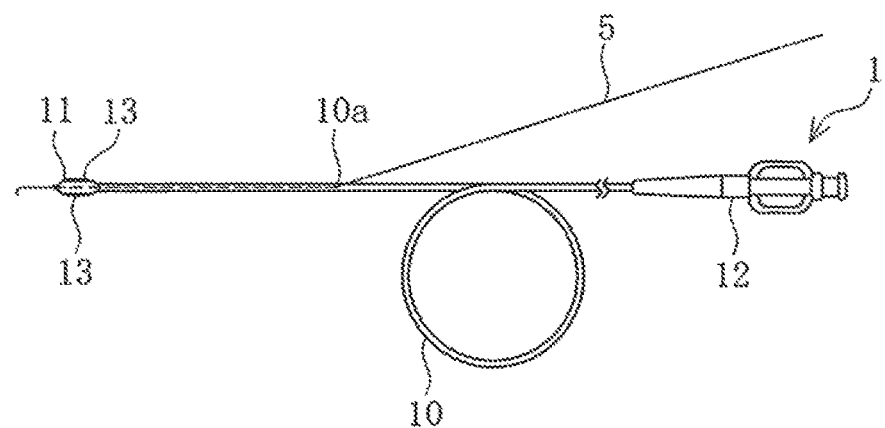
FIG. 1 is a front view of a medical device.

Hereinafter, embodiments of the present invention will be described with reference to the figures. Note that a dimension ratio in the figures is enlarged depending on the description and the ratio is different from an actual ratio in some cases. Note that, in this specification, a side, on which insertion of the medical device into a body lumen is performed, is referred to as a "distal end" or a "distal side", and a hand side, on which an operation is performed, is referred to as a "proximal end" or a "proximal side".

A medical device system of the embodiment includes: a medical device 1 that performs medical treatment on a lesion area in a blood vessel; a guide wire 5 that is used for the medical device 1; an anchor device 2 that fixes a distal portion of the guide wire 5 to the inside of the blood vessel, an anchor-device guide wire 6 that is used for the anchor device 2, a guiding catheter 3 that introduces the medical device 1 and the anchor device 2 inside the blood vessel, and a proximal-end fixing member 4 that fixes the guiding catheter 3 and the guide wire 5 when the position of the guide wire 5 is changed, such that the guide wire 5 can move in an insertion/pulling-out direction. The medical device 1 of the embodiment is used in percutaneous transluminal coronary angioplasty for medical treatment of the lesion area on a coronary artery in the heart.

Figure 2:
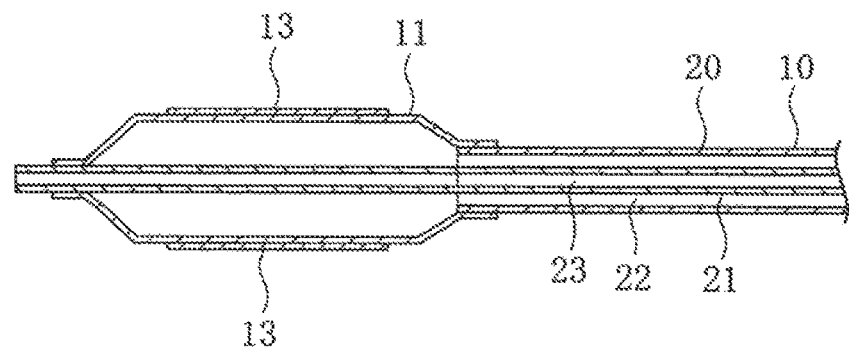
FIG. 2 is a longitudinal-sectional view of a distal portion of the medical device.

First, the medical device 1 is described. The medical device 1 is a scoring balloon catheter that widens a calcified lesion area in a blood vessel. As illustrated in FIG. 1, the medical device 1 includes a catheter shaft 10 having an elongated shape, a scoring balloon 11 that is provided in a distal portion of the catheter shaft 10, and a hub 12 that is provided in a proximal portion of the catheter shaft 10. As illustrated in FIG. 2, the catheter shaft 10 is disposed to be concentric with an outer tube 20 and an inner tube 21 which are formed to have elongated hollow shapes, respectively. The inner diameter of the outer tube 20 is larger than an outer diameter of the inner tube 21, and the inner tube 21 is accommodated in an inner hollow portion of the outer tube 20. The inner hollow portion of the inner tube 21 forms a guide wire lumen 23 into which the guide wire 5 is inserted. In addition, a dilation lumen 22 is formed in the inner hollow portion of the outer tube 20, and a dilating fluid of the balloon 11 is circulated through the dilation lumen on an outer side of the inner tube 21.

The guide wire 5 is inserted into the guide wire lumen 23 from an opening portion 10a at an intermediate position of the catheter shaft 10 in an axial direction. The inner tube 21 is provided only on the distal side from the opening portion 10a. The medical device 1 is a so-called rapid exchange type of catheter.

The inner tube 21 projects from the distal end of the outer tube 20 toward the distal side. A proximal-side end portion of the balloon 11 is fixed to a distal portion of the outer tube 20, and a distal-side end portion thereof is fixed to a distal portion of the inner tube 21. In this manner, the inside of the balloon 11 communicates with the dilation lumen 22. The balloon 11 is dilated with the dilating fluid that is injected therein via the dilation lumen 22. The dilating fluid may be a gas or a liquid. For example, it is possible to use a gas such as helium gas, a $CO_2$ gas, or $O_2$ gas, or a liquid such as a physiological salt solution or a contrast agent.

It is preferable that the outer tube 20 and the inner tube 21 are made of a material having a certain degree of flexibility. Examples of such materials include polyethylene, polypropylene, polybutene, ethylene-propylene copolymer, ethylene-vinyl acetate copolymer, an ionomer, or a mixture of two or more thereof such as a polyolefin, soft polyvinyl chloride resin, polyamide, polyamide elastomer, polyester, polyester elastomer, polyurethane, fluororesin such as polytetrafluoroethylene, silicone rubber, or latex rubber.

The scoring balloon 11 is made of a material having the flexibility, similar to the outer tube 20 or the inner tube 21. The scoring balloon 11 is provided with a metal blade 13 on a front surface of the scoring balloon. The blade 13 can approach the calcified lesion area and produce cracks therein during the dilation of the scoring balloon 11.

Figure 3:
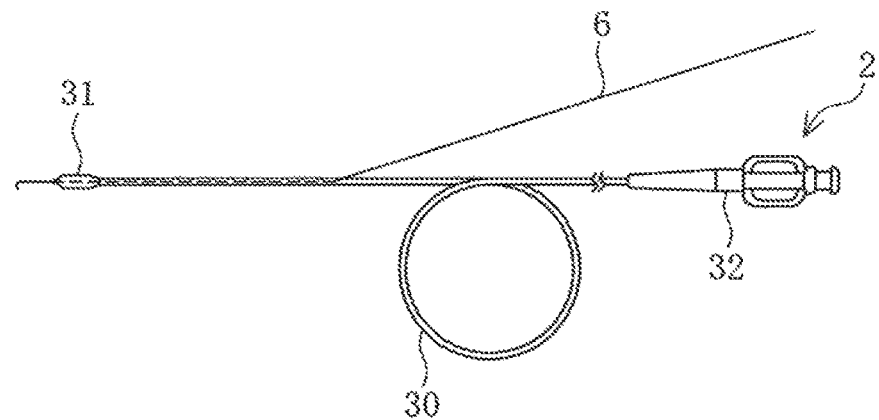
FIG. 3 is a front view of an anchor device.

Next, the anchor device 2 will be described. As illustrated in FIG. 3, the anchor device 2 is a balloon catheter. The balloon catheter includes an anchor catheter shaft 30 having an elongated shape, an anchor portion 31 as a balloon provided in a distal portion or the anchor catheter shaft 30, and an anchor catheter hub 32 provided in a proximal portion of the anchor catheter shaft 30. The anchor device 2 has the same structure as the medical device 1 except that the anchor portion 31 is a balloon without a blade.

Figure 4:
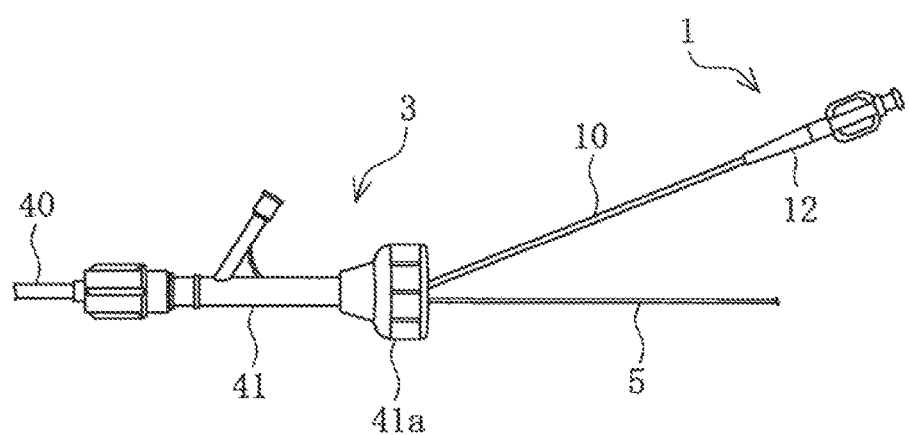
FIG. 4 is a front view of a proximal portion of a guiding catheter.

Next, the guiding catheter 3 will be described. As illustrated in FIG. 4, the guiding catheter 3 includes a shaft 40 that is inserted into a blood vessel and a port member 41 as an insertion opening of the medical device 1 or the like into the blood vessel. The shaft 40 has an inner diameter to the extent that it is possible to insert the medical device 1 and the guide wire 5 thereinto. The port member 41 is a common Y connector and is provided with a proximal-end insertion portion 41a in a proximal portion thereof, into which the medical device 1 or the guide wire 5 is inserted.

Figure 5:
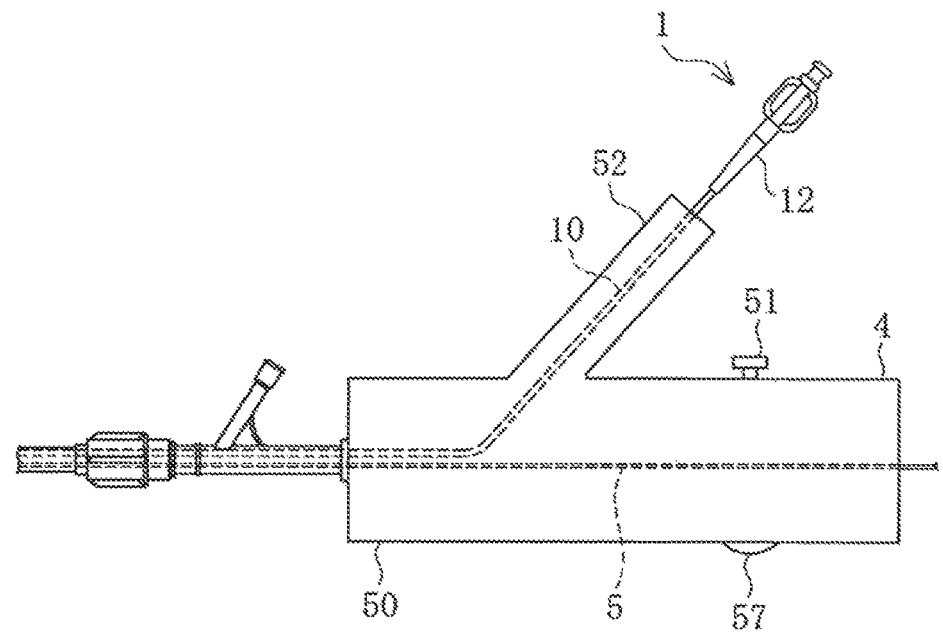
FIG. 5 is a front view of the proximal portion of the guiding catheter attached to a proximal-end fixing member.

As illustrated in FIG. 5, the proximal-end fixing member 4 is provided with a port-member fixing portion 50 that covers and fixes the proximal-end insertion portion 41a of the port member 41. In addition, the proximal-end fixing member 4 is provided with a guide-wire fixing portion 51 that fixes a portion of the guide wire 5 on the proximal side from the port member 41, and a medical-device guiding portion 52 into which a portion of the medical device 1 on the proximal side from the port member 41 is inserted.

Figure 6:
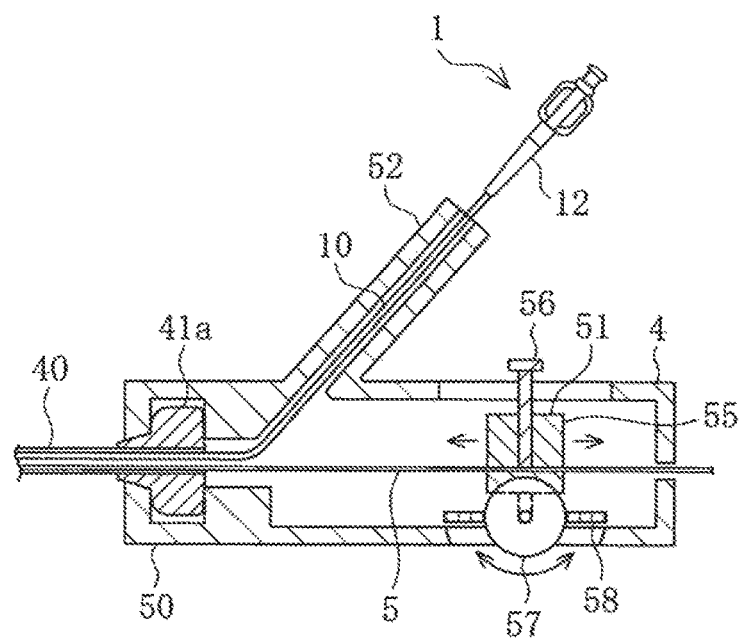
FIG. 6 is a longitudinal-sectional view of the proximal-end fixing member.

As illustrated in FIG. 6, the port-member fixing portion 50 has an inner shape that is substantially fitted in an outer shape of the proximal-end insertion portion 41a of the port member 41 so as to hold and fix the port member 41. The medical-device guiding portion 52 is formed to have a hollow pipe shape toward a direction different from that of a guide-wire fixing portion 51 such that a proximal portion of the medical device 1 that is inserted into the port member 41 is pulled out in a direction different from that of the guide wire 5.

The guide-wire fixing portion 51 has a hollow shape and the inside thereof is provided with a holding portion 55 into which the guide wire 5 is inserted and a pressing screw 56 as a screw-shaped member that is screwed to the holding portion 55. The pressing screw 56 is brought into pressure contact with the guide wire 5 inserted into the holding portion 55, by screwing of the screw and it is possible to fix the guide wire 5 to the holding portion 55 in the axial direction.

The holding portion 55 is linked to the operation unit 57 that can be subjected to rotary operation. The operation unit 57 is a member having a disk or columnar shape and a part of the operation unit is exposed outside of the proximal-end fixing member 4. Therefore, it is possible for the operator who grips the proximal-end fixing member 4 to perform a rotary operation of the operation unit 57. The operation unit 57 is also linked to a moving mechanism 58 and it is possible for the guide wire 5 to move in the axial direction in response to the rotary operation. As the operation unit 57 moves, the holding portion 55 linked to the operation unit 57 also moves in the axial direction of the guide wire 5. In other words, an operator performs the rotary operation of the operation unit 57 so as to move the guide wire 5 with respect to the blood vessel in the insertion/pulling-out direction. Since the guide wire 5 moves in response to the rotary operation of the operation unit 57, it is possible for the operator to perform fine adjustment such that it is possible to easily change a path of the guide wire 5 in the blood vessel, which will be described below.

Figure 7:
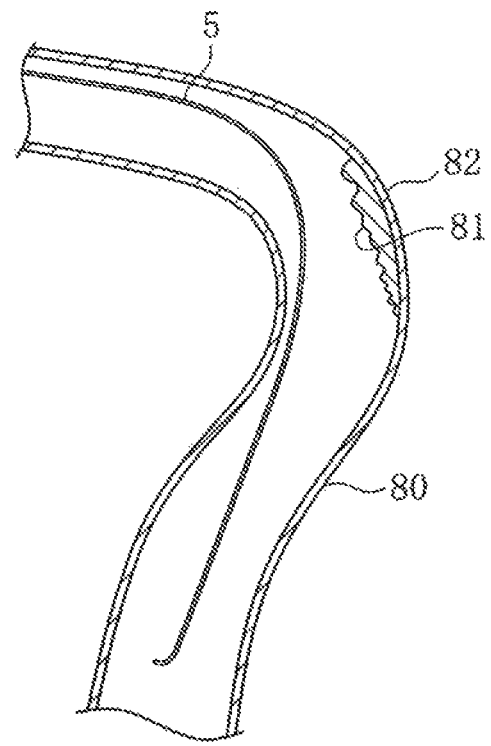
FIG. 7 is a longitudinal-sectional view of the vicinity of a lesion area viewed in a state in which the guide wire is inserted into a bent portion of a coronary artery.

Next, a position adjusting method of the medical device 1 in the blood vessel will be described. First, the guiding catheter 3 is inserted into the blood vessel from an appropriate position of an arm or the like and a distal portion of the shaft 40 is caused to approach an entrance of a coronary artery 80 while the guide wire 5 moves ahead. Then, as illustrated in FIG. 7, the guide wire 5 is caused to approach a position farther forward than a lesion area 81 of the coronary artery 80. In this example, the lesion area 81 is a calcified site on an inner wall surface of the coronary artery and is positioned on an outer curved side of a bent portion 82 of the coronary artery 80.

Figure 8:
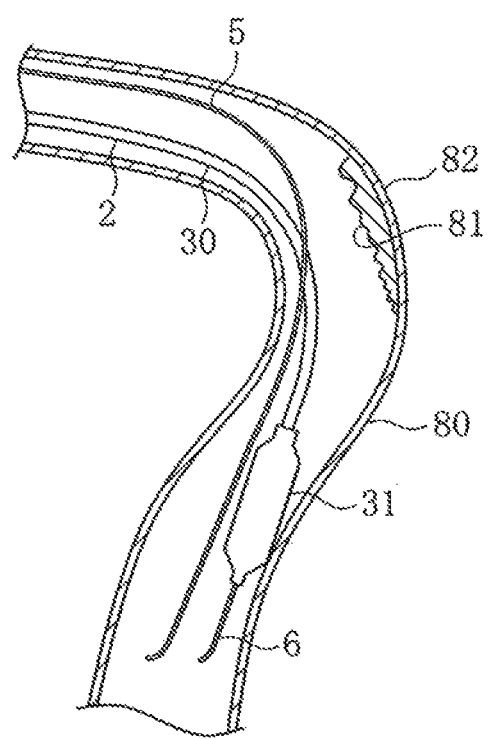
FIG. 8 is a longitudinal-sectional view of the vicinity of the lesion area viewed in a state in which the anchor device is inserted farther forward than the lesion area.

Next, similar to the guide wire 5, the anchor-device guide wire 6 is caused to approach a position farther forward than the lesion area 81 of the coronary artery 80. Subsequently, the anchor device 2 is inserted into the blood vessel, as illustrated in FIG. 8, and the anchor portion 31 is caused to approach a position farther forward than the lesion area 81 of the coronary artery 80.

Figure 9:
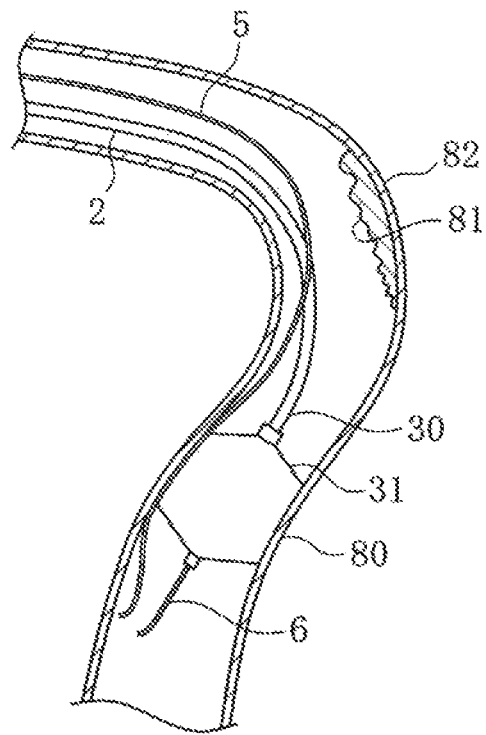
FIG. 9 is a longitudinal-sectional view of the vicinity of the lesion area viewed in a state in which the anchor device is dilated.

Here, as illustrated in FIG. 9, the anchor portion 31 of the anchor device 2 is dilated. The anchor portion 31 is dilated to have the same size as an inner diameter of the coronary artery 80 and the guide wire 5 is pushed to the inner wall surface of the coronary artery 80. In this manner, the distal portion of the guide wire 5 positioned farther forward than the lesion area 81 is fixed to the coronary artery 80.

Next, the medical device 1 is inserted into the blood vessel from the port member 41. The medical device 1 is inserted while being guided by the guide wire 5. The medical device 1 is inserted until the scoring balloon 11 approaches the position of the lesion area 81 of the coronary artery 80. In the state in FIG. 9, the guide wire 5 passes an inner curved side of the bent portion 82. Therefore, as represented by a dashed line in FIG. 10, the scoring balloon 11 inserted to the position of the lesion area 81 is also positioned on the inner curved side of the bent portion 82 in the coronary artery 80.

Figure 10:
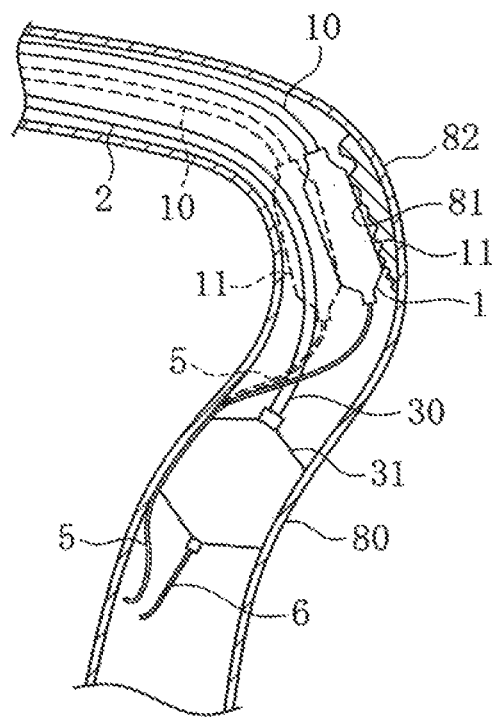
FIG. 10 is a longitudinal-sectional view of the vicinity of the lesion area viewed in a state in which the medical device is inserted into the lesion area and positional adjustment of a scoring balloon is performed.

In a case where it is not possible to effectively produce cracks in the lesion area 81 even when the scoring balloon 11 is dilated at a position of the dashed line in FIG. 10, the proximal-end fixing member 4 is attached to the port member 41 and the guide wire 5 is fixed to the proximal-end fixing member 4, as illustrated in a change from the state in FIG. 4 to the state in FIG. 5. In this manner, the distal portion of the guide wire 5 is fixed to the blood vessel by the anchor portion 31, and the proximal portion thereof is fixed to the port member 41 by the proximal-end fixing member 4.

Moreover, the operator performs the rotary operation of the operation unit 57 of the proximal-end fixing member 4, thereby making it possible to move the guide wire 5 in the insertion/pulling-out direction of the blood vessel. Since the distal portion of the guide wire 5 is fixed to the intravascular wall surface by the anchor portion 31, the path of the guide wire 5 changes in the bent portion 82 when the guide wire 5 is caused to move in the insertion/pulling-out direction of the blood vessel. Specifically, when the operator causes the guide wire 5 to move in the insertion direction of the blood vessel, the guide wire 5 moves from the inner curved side to the outer curved side of the bent portion 82 as represented by a solid line in FIG. 10. Depending on the movement, the scoring balloon 11 that is guided by the guide wire 5 also moves from the inner curved side to the outer curved side in the bent portion 82. When the operator causes the guide wire 5 to move in the pulling-out direction of the blood vessel, the guide wire 5 moves from the outer curved side to the inner curved side in the bent portion 82 and the scoring balloon 11 also moves from the outer curved side to the inner curved side in the bent portion 82. Until the scoring balloon 11 is appropriately positioned in the blood vessel, the positional adjustment continues through the operation of the operation unit 57.

Figure 11:
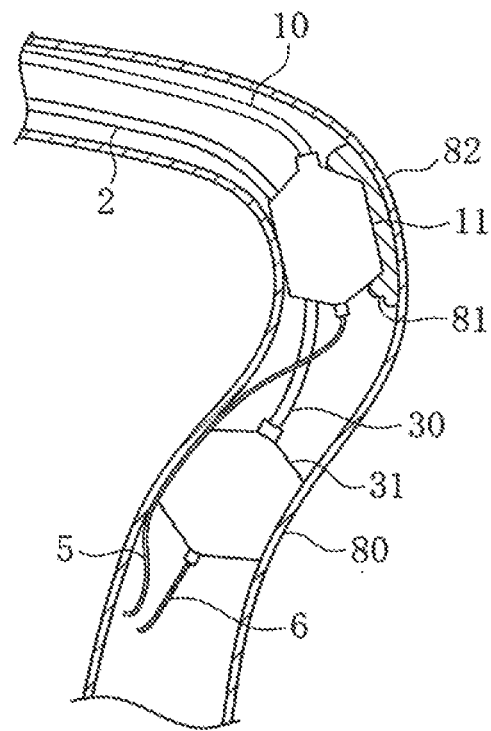
FIG. 11 is a longitudinal-sectional view of the vicinity of the lesion area viewed in a state in which the scoring balloon of the medical device is dilated.

After the position of the guide wire 5 is changed by the operation unit 57 and the position of the medical device 1 is adjusted to an appropriate position in the blood vessel, the scoring balloon 11 is dilated as illustrated in FIG. 11 and cracks are produced in the lesion area 81 by the blade 13. After appropriate medical treatment is performed on the lesion area 81, the scoring balloon 11 is deflated to be pulled out from the blood vessel, then the anchor portion 31 is deflated to be pulled out from the blood vessel, and the medical device 1 and the anchor device 2 are collected. Further, the guide wire 5 and the anchor-device guide wire 6 are also pulled out from the blood vessel and are collected.

In the embodiment, the medical device 1 includes the scoring balloon 11; however, another device may be included as long as the medical treatment is performed on the calcified lesion area by using the device. For example, a medical device that is provided with a cutter that rotates at a high speed, a rotary file, a transducer, a laser cutter on the distal portion of the device may be used, instead of the scoring balloon 11. Also in this case, the guide wire 5 is caused to move by the operation unit 57, and thereby it is possible to appropriately adjust the position of the medical device.

Next, a second embodiment of a position adjusting method of a medical device 7 in the blood vessel will be described. In the embodiment, the medical device 7 is an image diagnosis catheter and is inserted into the blood vessel in order to diagnose a state of a stent 60 that indwells in the lesion area 81 of the bent portion 82 of the coronary artery 80. Also in the embodiment, the guiding catheter 3 is inserted into the blood vessel and the distal portion of the shaft 40 is caused to approach an entrance of the coronary artery 80. Then, the guide wire 5 and the anchor-device guide wire 6 are caused to approach a position farther forward than the stent 60 that indwells in the coronary artery 80 and the anchor device 2 is inserted into the blood vessel. The anchor portion 31 is dilated at the position farther forward than the stent 60 and the distal portion of the guide wire 5 is fixed to the intravascular wall surface. Note that, since the anchor portion 31 is very short, there is a low possibility that the anchor portion is caught on the stent 60 during the insertion.

Figure 12:
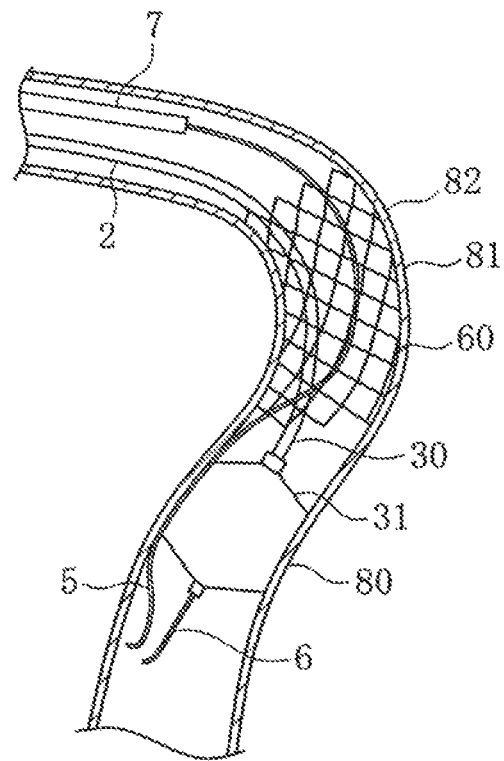
FIG. 12 is a longitudinal-sectional view of the vicinity of a lesion area viewed in a state in which a guide wire and an anchor device are inserted farther forward than the lesion area in which a stent indwells, an anchor portion is dilated, and the medical device is inserted to the vicinity in front of the stent, in a second embodiment.

Since the anchor portion 31 is dilated at the position farther forward than the stent 60, as illustrated in FIG. 12, the distal portion of the medical device 7 is inserted to a position in the vicinity in front of the stent 60 in the lesion area 81. In this example, the guide wire 5 moves through a position closer to the outer curved side of the bent portion 82, and there is a possibility that the distal portion of the medical device 7 will be caught on the stent 60 as is. In the hand side, the proximal-end fixing member 4 is attached to the port member 41, the guide wire 5 is fixed to the proximal-end fixing member 4, and it is possible for the guide wire 5 to move in the insertion/pulling-out direction by using the operation unit 57, and thereby the positional adjustment of the medical device 7 is performed.

Figure 13:
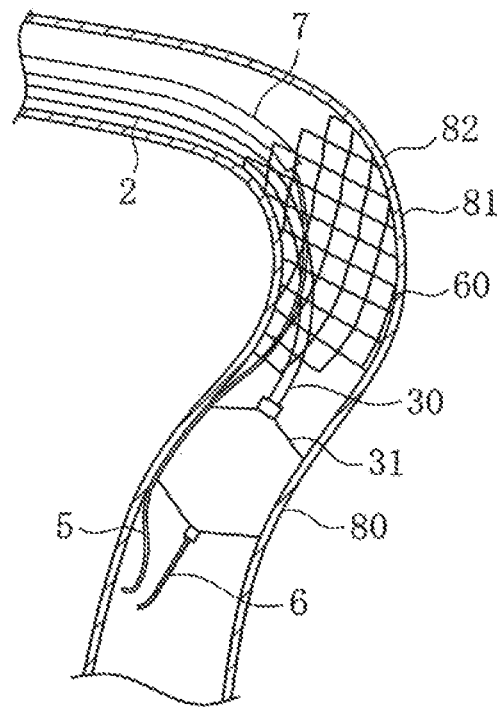
FIG. 13 is a longitudinal-sectional view of the vicinity of the lesion area viewed in a state in which the guide wire is caused to move to an inner curved side of a bent portion and the medical device approaches the inside of the stent.

The guide wire 5 is caused to move in the pulling-out direction of the blood vessel by using the operation unit 57, and thereby, as illustrated in FIG. 13, the guide wire 5 moves from the outer curved side to the inner curved side in the bent portion 82 such that an insertion path of the medical device 7 can pass through the central portion of the bent portion 82. In this manner, it is possible for the medical device 7 not to be caught on the stent 60, and it is possible to appropriately perform image diagnosis. In addition, it is possible to also prevent a shift in the position of the stent 60 that occurs due to the medical device 7 being caught on the stent 60.

Figure 14:
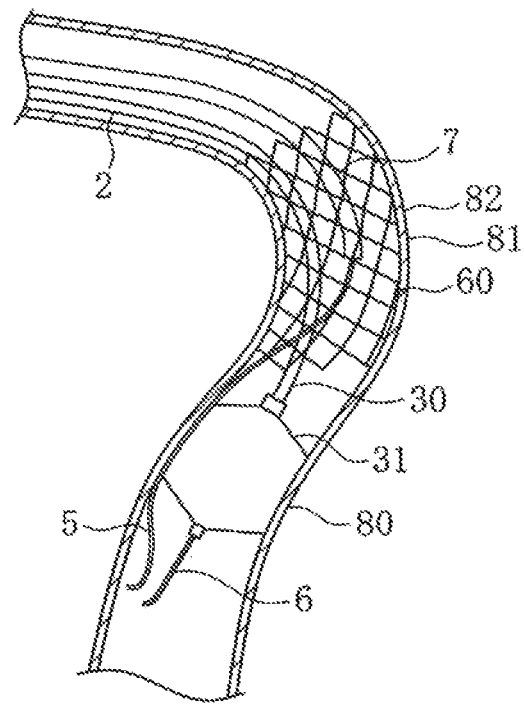
FIG. 14 is a longitudinal-sectional view of the vicinity of the lesion area viewed in a state in which the guide wire is caused to move to an outer curved side of the bent portion and the medical device approaches a distal portion of the stent.

In addition, in the state in FIG. 13, the guide wire 5 moves through a position closer to the inner curved side of the bent portion 82 in the vicinity of the distal portion of the stent 60. Also in a state in which the medical device 7 is disposed in the stent 60, the guide wire 5 is caused to move in the insertion direction of the blood vessel through the operation of the operation unit 57, and thereby, as illustrated in FIG. 14, the guide wire 5 moves to the outer curved side in the bent portion 82 such that the medical device 7 can pass through the central portion of the stent 60.

As described above, while the medical device 7 is inserted to the position of the stent 60 in the lesion area, it is possible to change the path of the guide wire 5 in the blood vessel through the operation of the operation unit 57.

Next, a third embodiment of a position adjusting method of a medical device 8 in the blood vessel will be described. In the embodiment, the medical device 8 includes, in the distal portion thereof, a balloon 71 provided with a second stent 70. The stent 60 indwells in the lesion area 81 of the bent portion 82 of the coronary artery 80 in advance. In the embodiment, in order to further dilate the stent 60, the second stent 70 is delivered to the lesion area by the medical device 8, the second stent is dilated, and an indwelling procedure in the lesion area 81 is performed.

Also in the embodiment, the guiding catheter 3 is inserted into the blood vessel and the distal portion of the shaft 40 is caused to approach an entrance of the coronary artery 80. Subsequently, the guide wire 5 and the anchor-device guide wire 6 are caused to approach a position farther forward than the stent 60 that indwells in the lesion area 81 of the coronary artery 80. Next, the anchor device 2 is inserted into the blood vessel, the anchor portion 31 is dilated at the position farther forward than the stent 60, and the distal portion of the guide wire 5 is fixed to the intravascular wall surface.

Figure 15:
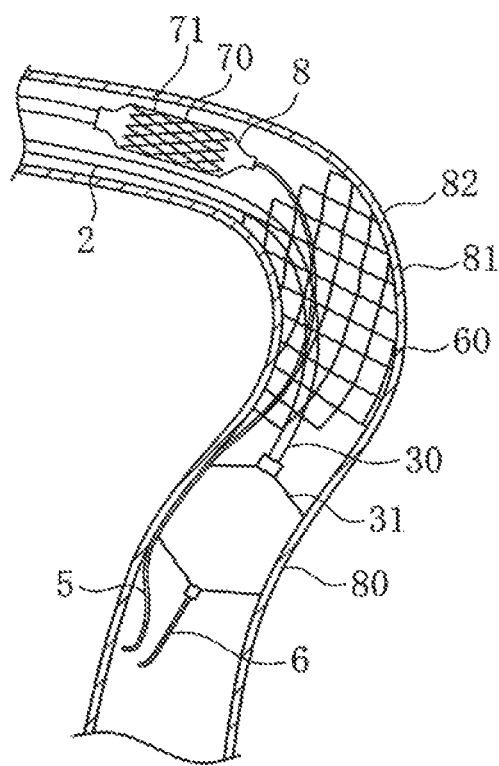
FIG. 15 is a longitudinal-sectional view of the vicinity of a lesion area viewed in a state in which a guide wire and an anchor device are inserted farther forward than the lesion area in which a stent indwells, an anchor portion is dilated, and the medical device is inserted to the vicinity in front of the stent, in a third embodiment.
Figure 16:
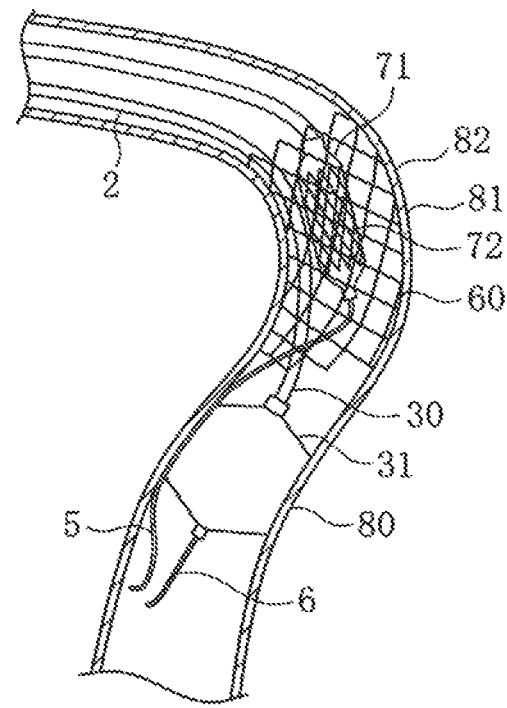
FIG. 16 is a longitudinal-sectional view of the vicinity of the lesion area viewed in a state in which the guide wire is caused to move to an outer curved side of a bent portion and the medical device approaches the inside of the stent.

Since the anchor portion 31 is dilated at the position farther forward than the stent 60, as illustrated in FIG. 15, the distal portion of the medical device 8 is inserted to a position in the vicinity in front of the stent 60 in the lesion area 81. In the hand side, the proximal-end fixing member 4 is attached to the port member 41, the guide wire 5 is fixed to the proximal-end fixing member 4, it is possible for the guide wire 5 to move in the insertion/pulling-out direction of the blood vessel by using the operation unit 57, and the positional adjustment of the medical device 8 is performed. In this example, since the guide wire 5 moves to be closer to the inner curved side of the bent portion 82, the guide wire 5 is caused to move in the insertion direction of the blood vessel by using the operation unit 57, and the guide wire 5 moves to the outer curved side in the bent portion 82. In this manner, the positional adjustment is performed such that the balloon 71 and the second stent 70 are positioned in the central portion of the stent 60. In this manner, it is possible to perform the insertion without the balloon 71 and the second stent 70 being caught on the stent 60.

Figure 17:
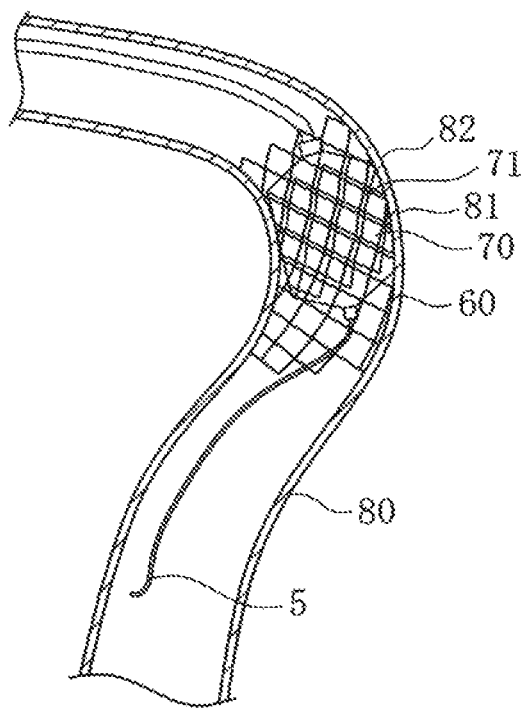
FIG. 17 is a longitudinal-sectional view of the vicinity of the lesion area viewed in a state in which a second stent provided in the medical device is expanded after the anchor device is collected.

In the embodiment, since the anchor device 2 and the anchor-device guide wire 6, which are inserted to the position farther forward than the lesion area, interfere with the dilation of the second stent 70, the anchor device and the anchor-device guide wire are collected before the second stent 70 is dilated. In other words, since the second stent 70 is disposed in the bent portion 82, the anchor portion 31 of the anchor device 2 is deflated and the anchor device 2 and the anchor-device guide wire 6 are pulled out from the blood vessel and are collected. Moreover, as illustrated in FIG. 17, the balloon 71 of the medical device 8 is dilated and the second stent 70 is also dilated. Since the second stent 70 is dilated, the balloon 71 is deflated and the medical device 8 and the guide wire 5 are pulled out and collected while the second stent 70 indwells in the bent portion 82 as is.

As described above, for a post device for dilating the stent 60 again, the guide wire 5 is caused to move by the operation unit 57 such that it is possible to perform positional adjustment of the balloon 71 and the second stent 70. In the embodiment, the second stent 70 is used to dilate the stent 60 again; however, the stent 60 may be dilated again with a dilation force of the balloon 71 without using the second stent 70. In this case, the anchor device 2 and the anchor-device guide wire 6 may be collected before the balloon 71 is dilated or may be collected after the balloon 71 is dilated.

As described above, the medical-device position adjusting method of adjusting the position of the medical device 1 by adjusting the path of the guide wire 5 inserted into the body lumen in the embodiment described above, the method including: a step of preparing the medical device 1 that is delivered to the lesion area 81 in the body lumen, the guide wire 5 that guides the medical device 1, the port member 41 that introduces the guide wire 5 and the medical device 1 into a living body, the proximal-end fixing member 4 that fixes the guide wire 5 and the port member 41 and is provided with the operation unit 57 that causes the guide wire 5 to move in an insertion/pulling-out direction from the fixed state, the anchor device 2 provided with the anchor portion 31 in the distal portion thereof, and the anchor-device guide wire 6 that guides the anchor device 2; a step of inserting the guide wire 5 from the port member 41 farther forward than the lesion area 81 of the body lumen; a step of inserting the anchor device 2 into the body lumen and fixing the guide wire 5 to the inner wall surface of the body lumen by the anchor portion 31 at the position farther forward than the lesion area 81; a step of inserting the medical device 1 from the port member 41 along the guide wire 5 into the lesion area 81 or a position in the vicinity of the lesion area 81; and a step of fixing the guide wire 5 and the port member 41 with the proximal-end fixing member 4, causing the guide wire 5 to move in the insertion/pulling-out direction by using the operation unit 57, thereby, changing the path of the guide wire 5 in the body lumen, and adjusting the position of the medical device 1 in the lesion area 81. In this manner, it is possible to cause the guide wire 5 to move to a hand-side position in the body lumen, and thus it is possible to adjust the position of the medical device 1 to the appropriate position in the body lumen. In other words, in the medical-device position adjusting method, since it is possible to adjust the position of the medical device 1 such that it is possible to exhibit the best performance of the medical device, and it is possible to smoothly insert the medical device 1 to a desired position, it is possible to achieve improvement of efficacy of medical treatment and shortening of time for medical treatment.

In addition, in the medical-device position adjusting method of the embodiment described above, the lesion area 81 is positioned in the bent portion 82 of the body lumen. The guide wire 5 is caused to move in the insertion/pulling-out direction by the operation unit 57, and thereby the path of the guide wire 5 is changed between the outer curved side and the inner curved side of the bent portion 82. In this manner, it is possible to reliably adjust the position of the medical device 1 in the bent portion of the body lumen in which it is difficult to appropriately position the medical device 1.

In addition, in the medical-device position adjusting method of the embodiment described above, in the step of inserting the medical device 1 from the port member 41 along the guide wire 5, the medical device 7 is inserted to the position in the vicinity in front of the lesion area 81. In the step of adjusting the position of the medical device 7 in the lesion area 81, the path of the guide wire 5 is changed in the body lumen while the medical device 7 is inserted to the position of the lesion area 81. In this manner, it is possible to perform the insertion into the body lumen while the medical device 7 is disposed at an appropriate position.

In addition, in the medical-device position adjusting method of the embodiment described above, the anchor portion 31 as the balloon is dilated in the body lumen, and the dilation of the balloon causes the guide wire 5 to be fixed to the inner wall surface of the body lumen. The method further includes a step of deflating and pulling out the anchor portion 31 from the body lumen, after the step of changing the path of the guide wire 5 in the body lumen and adjusting the position of the medical device 1 in the lesion area 81. In this manner, it is possible to perform a function of fixing the guide wire 5 in a simplified structure, and it is possible to easily collect the anchor portion 31 from the lesion area 81.

In addition, the medical-device position adjusting method of the embodiment described above further includes a step of causing the medical device 8 to function in the lesion area, after the step of deflating and pulling out the anchor portion 31 from the body lumen. In this manner, it is possible for the anchor device 2 not to interfere with the function of the medical device 8.

In addition, the medical device system of the embodiment described above includes the medical device 1 that is delivered to the lesion area 81 in the body lumen, the guide wire 5 that guides the medical device 1, the port member 41 that introduces the guide wire 5 and the medical device 1 into the living body, the proximal-end fixing member 4 that fixes the guide wire 5 and the port member 41 and is provided with the operation unit 57 that causes the guide wire 5 to move in the insertion/pulling-out direction from the fixed state, the anchor device 2 provided with the anchor portion 31 in the distal portion thereof, and the anchor-device guide wire 6 that guides the anchor device 2. According to the medical device system, it is possible to cause the guide wire 5 to move to the hand-side position in the body lumen, and thus it is possible to adjust the position of the medical device 1 to the appropriate position in the body lumen. In other words, in the medical device system, since it is possible to adjust the position of the medical device such that it is possible to exhibit the best performance of the medical device 1, and it is possible to smoothly insert the medical device 1 to the desired position, it is possible to achieve improvement of efficacy of medical treatment and shortening of time for medical treatment.

In addition, in the medical device system of the embodiment described above, the proximal-end fixing member 4 is provided with the port-member fixing portion 50 to which the port member 41 is fixed, a guide-wire fixing portion 51 to which the guide wire 5 is fixed, and the medical-device guiding portion 52 that guides the medical device 1 out in a direction different from the insertion/pulling-out direction of the guide wire 5. In this manner, it is possible not to interfere with the insertion of the medical device 1 while the port member 41 and the guide wire 5 are fixed.

In addition, in the medical device system of the embodiment described above, the guide-wire fixing portion 51 is provided with a holding portion 55 that holds and fixes the guide wire 5, and the operation unit 57 that causes the holding portion 55 to move in the insertion/pulling-out direction with respect to the port member 41. In this manner, the operator can cause the guide wire 5 to move in the insertion/pulling-out direction through the operation of the operation unit 57, and it is possible to reliably perform fine adjustment of the movement of the guide wire 5.

Note that the present invention is not limited to the embodiments described above, and it is possible for those skilled in the art to perform various modifications without departing from the spirit and the scope of the invention. For example, in the embodiments described above, the medical device is used for the lesion area in the coronary artery of the heart; however, the medical device may be used for a lesion area in a body lumen other than the coronary artery. In addition, in the embodiments described above, the position of the guide wire is changed in the bent portion of the blood vessel; however, it is possible to change the position of the guide wire at any position in the body lumen. In addition, types of medical devices which are subjected to the positional adjustment are not limited to the medical devices described above.

What is claimed is:

1. A medical device system comprising:
   a medical device that is configured to be delivered to a lesion area in a body lumen;
   a guide wire that is configured to guide the medical device;
   a port member that is configured to introduce the guide wire and the medical device into a living body;
   a proximal-end fixing member that is configured to fix the guide wire and the port member and is provided with an operation unit that is configured to cause the guide wire to move in an insertion/pulling-out direction from the fixed state;
   an anchor device provided with an anchor portion in a distal portion thereof; and
   an anchor-device guide wire that is configured to guide the anchor device.

2. The medical device system according to claim 1, wherein the proximal-end fixing member is provided with a port-member fixing portion to which the port member is fixed, a guide-wire fixing portion to which the guide wire is fixed, and a medical-device guiding portion that is configured to guide the medical device out in a direction different from the insertion/pulling-out direction of the guide wire.

3. The medical device system according to claim 2, wherein the guide-wire fixing portion is provided with a holding portion that is configured to hold and fix the guide wire, and the operation unit that causes the holding portion to move in the insertion/pulling-out direction with respect to the port member.

4. The medical device system according to claim 1, wherein the anchor portion comprises a balloon that is configured to be dilated to fix the position of a portion of the guide wire relative to the body lumen.

5. The medical-device system according to claim 1, wherein the medical device comprises a bladed balloon.

6. A medical device system comprising:
   a medical device that is configured to be delivered to an area in a body lumen;
   a guide wire that is configured to guide the medical device in the body lumen to the area;
   an anchor device provided with an anchor portion in a distal portion thereof;
   an anchor-device guide wire that is configured to guide the anchor device in the body lumen;
   a port member that is configured to introduce the guide wire and the medical device into the body lumen; and
   a proximal-end fixing member that is configured to fix the guide wire and the port member and is provided with an operation unit that is configured to cause the guide wire to move in an insertion/pulling-out direction from the fixed state,
   the anchor device being configured to fix an axial position of a distal portion of the guide wire relative to the body lumen.

7. The medical device system according to claim 6, wherein the proximal-end fixing member is provided with a port-member fixing portion to which the port member is fixed, a guide-wire fixing portion to which the guide wire is fixed, and a medical-device guiding portion that is configured to guide the medical device out in a direction different from the insertion/pulling-out direction of the guide wire.

8. The medical device system according to claim 7, wherein the guide-wire fixing portion is provided with a holding portion that is configured to hold and fixe the guide wire, and the operation unit that causes the holding portion to move in the insertion/pulling-out direction with respect to the port member.

9. The medical device system according to claim 6, wherein the anchor portion comprises a balloon that is configured to be dilated to fix the position of a portion of the guide wire relative to the body lumen.

10. The medical-device system according to claim 6, wherein the medical device comprises a bladed balloon.

* * * * *